United States Patent [19]

Kashman et al.

[11] Patent Number: 4,935,439

[45] Date of Patent: Jun. 19, 1990

[54] ANTIVIRAL COMPOSITIONS DERIVED FROM MARINE SPONGE EPIPOLASIS REISWIGI AND THEIR METHODS OF USE

[75] Inventors: Yoel Kashman; Shulamit Hirsch, both of Tel Aviv, Israel; Sue S. Cross, Ft. Pierce; Frank Koehn, Vero Beach, both of Fla.

[73] Assignee: Harbor Branch Oceanographic Institution, Inc., Ft. Pierce, Fla.

[21] Appl. No.: 91,078

[22] Filed: Aug. 31, 1987

[51] Int. Cl.$^5$ .................. A01N 43/20; A01N 37/02; A01N 35/00

[52] U.S. Cl. .................. 514/475; 514/546; 514/691

[58] Field of Search .................. 514/546, 691, 475

[56] References Cited

U.S. PATENT DOCUMENTS 4,576,961  3/1986  Lorck .................. 514/462
4,708,962 11/1987  Higa .................. 514/475

Primary Examiner—Douglas W. Robinson
Assistant Examiner—Russell Travers
Attorney, Agent, or Firm—Saliwanchik & Saliwanchik

[57] ABSTRACT

This invention relates to antiviral organic compositions and derivatives thereof; a process of producing the antiviral compositions; and a method for inhibiting viruses utilizing the compositions. More particularly, the compositions are derived from marine sponges of the genus Epipolasis.

4 Claims, No Drawings

ANTIVIRAL COMPOSITIONS DERIVED FROM MARINE SPONGE EPIPOLASIS REISWIGI AND THEIR METHODS OF USE

FIELD OF THE INVENTION

This invention relates to organic compounds which have useful antiviral activity. More particularly, this invention relates to methods of making and using organic antiviral compositions derived from the marine sponge Epipolasis

BACKGROUND OF THE INVENTION

Viral diseases afflict man, plants, insects, and animals. The prevention and control of viral diseases have important health and economic implications.

Viral diseases contribute to afflictions in humans including common colds, herpes, and cancer, and the importance of their control is obvious. It is important to control viral diseases in animals both for economic reasons and because animals can become virus reservoirs or carriers which facilitate the spreading of viral diseases to humans. Viral plant diseases have been known to disrupt the cultivation of fruit trees, tobacco, and various vegetables. Insect viral diseases are also of interest because of the insects' ability to transfer viral diseases to humans.

The prevention and control of viral diseases are thus of prime importance to man, and considerable research has been devoted to antiviral measures. Certain methods and chemical compositions have been developed which aid in inhibiting, controlling or destroying viruses. Nevertheless, additional methods and antiviral chemical compositions are needed.

A potential source for antiviral compositions is plant and animal life and of particular interest herein are marine sponges.

SUMMARY OF THE INVENTION

It is therefore an object of the invention to provide novel compositions which are useful as antiviral agents; antiviral methods of using the compositions; and a process for producing such compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described herein, the invention comprises antiviral compositions with the following formulae:

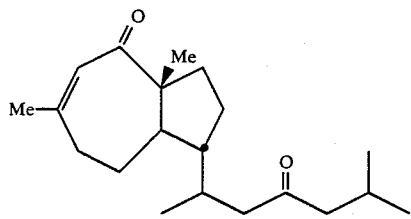
(I)

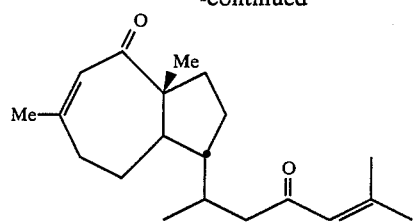
(II)

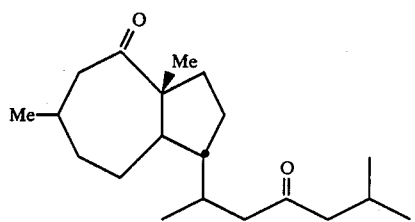
(III)

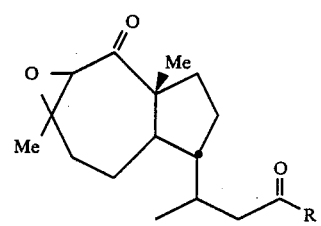
(IV)

where R =

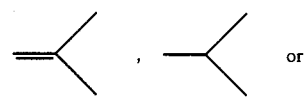

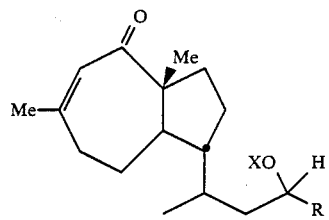
(V)

where R =

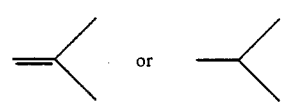

and X = H or OAc;

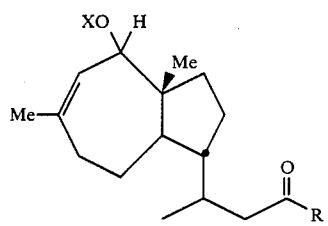
(VI)

where R =

-continued

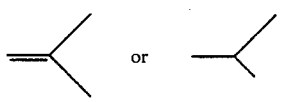

and X = H or OAc; and

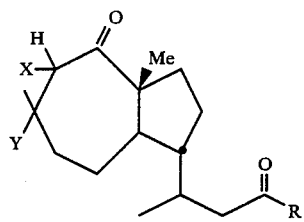 (VII)

where R =

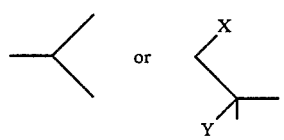

and X, Y = Br, Cl, OH or OAc.

In preferred embodiments of the invention, the compositions are substantially pure.

As embodied and fully described herein, the invention comprises antiviral compositions comprising, as its active ingredient, an effective antiviral amount of one or more compositions according to formulae I–VIII.

As embodied and fully described herein, the invention comprises a method for inhibiting viruses comprising contacting a virus with an effective antiviral amount of one or more compositions according to formulae I–VII.

It is to be understood that both the foregoing general and the following detailed description are merely exemplary and explanatory and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention an antiviral composition is provided comprising as active ingredient an effective antiviral amount of one or more of the compositions described above and identified by formulae:

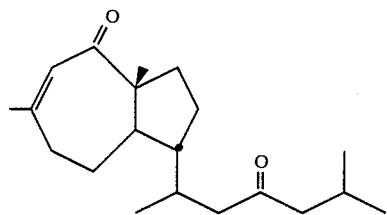 (I)

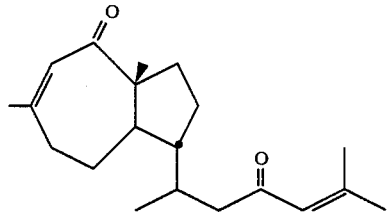 (II)

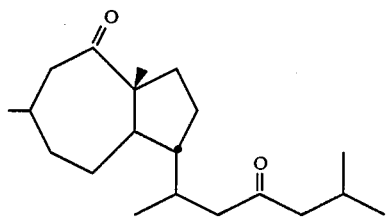 (III)

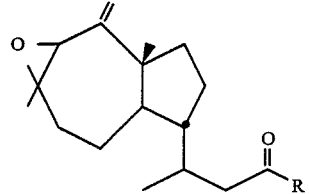 (IV)

where R =

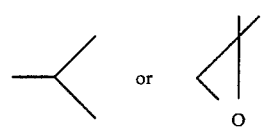

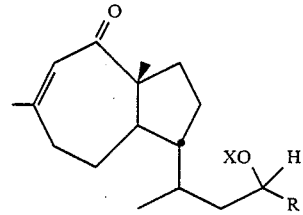 (V)

where R =

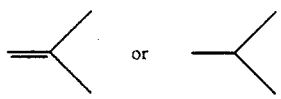

and X = H or OAc;

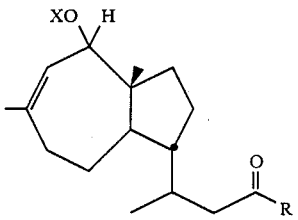 (VI)

where R =

-continued

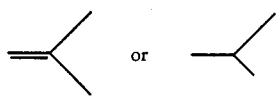

and X = H or OAc; and

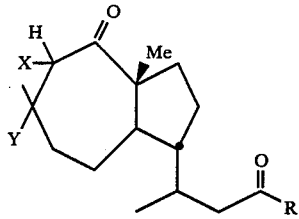
(VII)

where R =

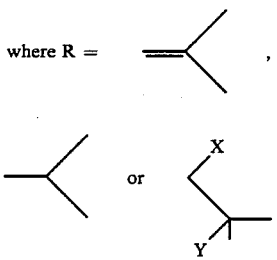

and X, Y = Br, Cl, OH or OAc.

In preferred embodiments of the invention, the compositions are substantially pure.

In more preferred embodiments of the invention, the invention comprises compositions of formulae I-VII and a non-toxic pharmaceutically acceptable carrier or diluent.

While effective amounts may vary, as conditions in which the antiviral compositions are used vary, a minimal dosage required for activity is generally between 2 and 20 micrograms against 25–100 infectious doses of virus. In accordance with the present invention, viruses are inhibited or killed by a method comprising contacting a virus with an effective antiviral amount of one or more compositions according to formulae I-VII. The minimal effective amount is generally from 2 to 20 micrograms against 25 to 100 infectious doses of virus. The compositions of formulae I-VII are active in inhibiting or killing both DNA and RNA viruses. Examples of such DNA viruses include herpes simplex types I and II ("HSV-I" and "HSV-II"), adenoviruses and papovaviruses. Examples of such RNA viruses include vesicular stomatitis viruses ("VSV"), arenaviruses, influenza viruses, retroviruses, coxsackieviruses, coronaviruses, rhinoviruses, and polioviruses. Useful examples of nontoxic pharmaceutically acceptable carriers or diluents include, but are not limited to, the following: ethanol, dimethyl sulfoxide, and glycerol.

The effectiveness of the compositions of the invention for inhibiting viruses indicates that the compositions of formulae I-VII should also be useful in controlling viral infections in host animals and plants which are caused by a virus which is thus inhibited or destroyed. Viral infections which may be controlled by utilizing compositions of the present invention include, but are not limited to, those caused by RNA viruses and DNA viruses described above. The invention may also be useful in controlling common viral infections of plants.

As embodied and fully described herein, the invention also comprises a new process to produce the compositions of formulae I-VII. A detailed description and explanation of a preferred embodiment of the process of the invention to produce the composition according to formulae I-VII is as follows.

A quantity of the marine sponge Epipolasis is collected, freeze dried, contacted with organic solvents and homogenized to form an extract. The extract is fractionated by chromotographic techniques to obtain certain fractions which are further fractionated and purified by chromatographic techniques into fractions which contain the desired compositions according to formulae I-VII. Specific compositions according to the invention are thus isolated by various chromatographic techniques from the fractions obtained.

The extract obtained from the organic solvent dichloromethane is presently preferred. Other suitable solvents may be substituted, however Suitable organic solvents include, but are not limited to, the following: heptane, hexane, isooctane, acetone, methanol, ethanol, isopropanol, toluene, benzene, diethyl ether, t-butylmethyl ether, chloroform, 1,2-dichloroethane, or any mixture thereof. Different ratios of solvent mixtures may be used for the solvent in the invention as would be known to those skilled in the art.

Any suitable fractionation and isolation techniques may be utilized in accordance with the process of the invention. Suitable fractionation techniques include various chromatographic techniques, such as flash chromatography using absorbents known to those skilled in the art (e.g., silica gel - H) eluted with a suitable solvent or series of solvents such as, for example, heptane, chloroform, methanol, hexanes, isooctane, dichloromethane, 1,2-dichloroethane, benzene, toluene, isopropanol, and diethyl ether or any mixture thereof, and/or high-pressure liquid chromatography with suitable columns as would be known to those skilled in the art (e.g., silica gel) eluted with a suitable solvent such as, for example, ethyl acetate and heptane and mixtures thereof.

It is therefore apparent that the compositions of the invention, the processes for producing the compositions of the invention and the methods for utilizing the compositions of the invention to inhibit viruses are effective for inhibiting or destroying viruses and therefore controlling diseases caused by or related to such viruses in fulfillment of the objects of the invention.

EXAMPLE

The invention will now be illustrated by an example. The example is not intended to limit the scope of the present invention. In conjunction with the detailed and general descriptions above, the example provides further understanding of the present invention and outlines a process for producing compositions of the invention.

The following example represents a preferred embodiment of the compositions, processes and methods of the invention for satisfying the stated objects of the invention. The starting materials and reagents in the examples whose method of preparation are not indicated are commercially available from sources known to the art such as chemical supply houses.

Samples of the marine sponge *Epipolasis reiswigi* were collected off the coast of the Bahama Islands at a depth of 330 meters. 250 grams of the sponge were freeze dried to yield a sample of 55 grams dry weight. This was extracted successively with heptane; 90% dichloromethane/10% methanol; 80% dichloromethane/20% methanol; 20% dichloromethane/80% methanol; and methanol. The dichloromethane extract, weighing 1.3 grams, was evaluated by antiviral disc assays for HSV-1, VSV, and A-59 viruses. A 200 μg/ml specimen gave the following results:

| HSV-1 | | VSV | | A-59 | |
|---|---|---|---|---|---|
| cyt | av | cyt | av | cyt | av |
| 16 | | 16 | | 0 | ++ |

This data indicated good antiviral activity, and the extract was further separated by flash chromatography on silica gel - H using heptane, methylene chloride and a 50% methylene chloride/50% methanol mixture as successive eluents. Ten fractions were obtained and were evaluated for antiviral activity. Fractions 1-6, containing olefinic compounds, had no antiviral activity. Similarly, no antiviral activity was detected in fractions 9-10. Fractions 7-8, containing a mixture of diterpenes, had the following activity:

| | HSV-1 | | VSV | | A-59 | |
|---|---|---|---|---|---|---|
| | cyt | av | cyt | av | cyt | av |
| 20 ug/ml | 16 | | 16 | | 0 | ++ |
| 2 ug/ml | 0 | ++ | 0 | ++ | 0 | — |

Fractions 7-8 were further purified by flash chromatography on silica gel - H eluted with heptane/10-20% ethyl acetate followed by high pressure liquid chromatography on a silica gel with a heptane/10-20% ethyl acetate mixture as the solvent. This yielded two fractions: A, weighing 500 mg, and B, weighing 40 mg. The fractions were tan colored oils. The major active component of these fractions were diterpenes A and B. Spectral analysis of A and B gave the following data:

Diterpene A

U.V. (Heptane): 223 nm ($\epsilon$2300), 205 nm ($\epsilon$5700).
I.R. (CHLCl$_3$): 2940br, 1700, 1630 cm$^{-1}$.
$^1$H NMR (360 MHz, CDCl$_3$): 5.85s(1H), 2.5dt(1H, J=18.3, 4.9), 2.44brd(1H, J=12.9), 2.38m(2H), 2.35d(1H, J=6.6), 2.33m(2H), 2.27brd(1H, J=14.5), 2.21dsept(1H, J=6.6, 0.6), 1.98s(3H), 1.96m(1H), 1.90m(1H), 1.85m(1H), 1.80m(1H), 1.74dd(1H, J=9.6, 1.6), 1.68ddd(1H, J=18.5, 6.5, 10.2, 2.7), 1.39m(1H), 1.20s(3H), 1.0d(6H, J=6.6), 0.98d(3H, J=6 6).
 total: 1=CH, 4-CH, 6-CH$_2$, 5-CH$_3$
$^{13}$C NMR (90MHz, CDCl$_3$): 210.4s, 206.9s, 152.4s, 127.1d, 56.5s, 52.6t, 47.9d, 45.4t, 45.3d, 35.2t, 34.8t, 29.6d, 28.5q, 24.7t, 24.6t, 22.6q, 22.5q, 22.2t, 20.1q, 19.8q.
 total: 1C=0, 1=C, 1-C, 1=CH, 4-CH, 6-CH$_2$, 5-CH$_3$
M.S. (HREI):m/z 304 (1.8%, 0.3ppm dev.),C$_{20}$H$_{32}$O$_2$ 286(3%), 249 (1.2%, 205 (7%), 178 (10%), 95(11%), 82(100%)
[α]$_D^{20}$=−10°(C=0.1, CHCl$_3$)

Diterpene B

U.V. (Heptane): 232 nm ($\epsilon$1800).
I.R. (CHLCl$_3$): 2900 br, 1650, 1605 cm$^{-1}$.
$^1$H NMR (360 MHz, CDCl$_3$): 6.04sht (1H, J=1.3), 5.82s(1H), 2.41m(2H), 2.27m(2H), 2.20m(1H), 2.13s(3H), 1.88s(6H), 1.82m(1H), 1.74m(1H), 1.68m(3H), 1.64dt (1H, J=9.3, 1.5), 1.32m (2H), 1.11s (3H), 0.93d (3H, J=6.5).
 total: 2=CH, 3-CH, 5-CH2, 5-CH$_3$
$^{13}$C NMR (90MHz, CDCl$_3$): 207.9s, 201.3s, 155.6s, 153.2s, 127.8d, 124.8d, 57.1s, 48.6d, 47.0T, 45.8d, 35.7t, 35.3t, 30.8d, 29.1q, 28.2q, 25.2t, 22.8t, 21.2q, 20.6q, 20.4q.
 total: 2C=0, 2=C, 1-C, 2=CH, 3-CH, 5-CH$_2$, 5-CH$_3$
M.S. (HREI): m/z 302(0.5%), C$_{20}$H$_{30}$O$_2$ 205 (13%), 178 (10%), 125 (28%), 83 (100%).
D(CHCl$_3$): −20°

| Me | Diterpene B | Diterpene A |
|---|---|---|
| 13 | 1.88s | 1.98s |
| 16 | 1.88s | 1.00dd |
| 17 | 2.13s | 0.98d |
| 19 | 0.93d | 1.00d |
| 20 | 1.11s | 1.20s |
| 4 | 5.82s | 5.58s |
| 14 | 6.04shd | 2.38m |

The structures of diterpenes A and B were determined by one dimensional and two dimensional NMR experiments:

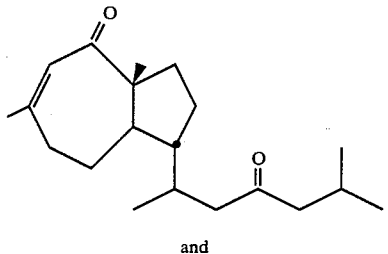

A (Formula I)

and

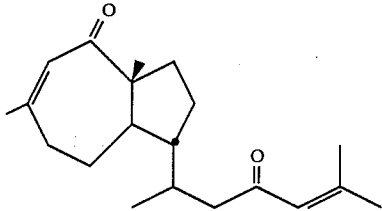

B (Formula II)

From the $^1$H and $^{13}$C NMR of diterpene B, 2D-COSY and 2D-CHCORR, in comparison to diterpene A, the inventors determined that diterpene B contains an additional double bond whose place in the molecule can be determined by comparing NMR signals for the methyl groups and olefinic protons in both diterpenes.

The antiviral activity of diterpene A and B is:

| | Diterpene A | | | | | |
|---|---|---|---|---|---|---|
| | HSV-1 | | VSV | | A-59 | |
| | cyt | av | cyt | av | cyt | av |
| 20 μg/ml | 16 | | 16 | | 0 | ++ |
| 2 μg/ml | 0 | +++ | 12 | +++ | 0 | — |
| | Diterpene B | | | | | |
| | HSV-1 | | VSV | | A-59 | |
| | cyt | av | cyt | av | cyt | av |
| 20 μg/ml | 16 | | 16 | | 0 | + |
| 2 μg/ml | 0 | — | 0 | — | 0 | — |

ANTIVIRAL ACTIVITIES OF THE COMPOSITIONS OF THE INVENTION

The following assay methods and essentially similar methods were utilized to demonstrate the in vitro antiviral effectiveness of diterpenes A and B as reported.

Antiviral Disc Assay for HSV-1 and VSV

A. MAINTENANCE OF CELL CULTURES
1. Virus
   a. Both herpes simplex type 1 (HSV-1) and vesicular stomatitis virus (VSV) replicate in the CV-1 cell line. CV-1 is a fibroblast-like cell culture derived from primary African green monkey cells.
2. Growth of CV-1 Cells
   a. Seed 150 cm² tissue culture flasks each with $10 \times 10^6$ CV-1 cells in 40 ml of EMEM with 10% FBS (growth medium).
   b. Seven days after seeding the flasks cell numbers should be approximately $40-50 \times 10^6$ cells. CV-1 cells have a doubling time of 72 hours based on these numbers.
3. Trypsinization
   a. Aseptically remove the medium.
   b. Rinse cell sheet with 10 ml of $Ca^{++}$ and $Mg^{++}$ free Dulbecco's phosphate buffered saline.
   c. Add 4.0 ml of trypsin - EDTA mixture.
   d. Incubate flask at room temperature with occasional rocking until the cells detach from the flask (about 5 min).
   e. Shake flask.
   f. Add 10 ml EMEM growth medium and break up cell clumps with pipetting.
   g. Count cells.

B. PREPARATION OF PLATES FOR VIRAL ASSAYS
1. Cell Concentration
   a. Dilute the cells with EMEM to $4 \times 10^5$ cells/ml.
   b. Seed 24 well trays with 0.5 ml per well. Cell concentration per well is $2 \times 10^5$ cells.
   c. Incubate at 37° C. with 5% $CO_2$.
   d. The wells can be used over the next several days beginning the day after seeding (preferably 2, 3, or 4).

C. ASSAY OF HSV-1 AND VSV IN CV-1 CELLS
1. Infection of CV-1 cells in plates with virus.
   a. Remove medium from wells.
   b. Infect well with at least 25 and no more than 80 plaque forming units (PFU) of virus.
   c. Incubate infected cells at 37° C. for 1.0 hours.
   d. Pour off supernatant at end of incubation period.
   e. Add 0.5 ml of methylcellulose overlay medium (MCO).
      (1) MCO is a maintenance medium, without phenol red, made with 1% 4000 centipoise methylcellulose. FBS is used at 5% level.
2. Drug Evaluation
   (a.) For drug evaluation wet filter paper discs (6 mm diameter) with approximately 0.02 ml of marine extract or test compound.
      (1) Allow solvent to evaporate for 20 to 30 minutes at room temperature.
      (2) Place discs in the well containing CV-1 cells, virus, and MCO.
   b. Incubate tissue culture plates for 48 hours at 37° C.
   c. After 48 hours place 0.5 ml NRMCO on each well.
      (1) NRMCO is a maintenance overlay medium, without phenol red, containing 0.1 mg neutral red dye per ml and 2% 15 centipoise methylcellulose.
      i. Neutral red solution prepare 200 x neutral red solution at 20 mg/ml in water. Sterilize by autoclaving. For 20 ml add 400 mg neutral red dye, at a concentration of 0.1 mg/ml.
      ii. NRMCO overlay medium:
      45 ml 2 X colorless medium (CM)
      5 ml FBS (or calf serum)
      50 ml 4% 15 centipoise methylcellulose (or 2% agar)
      0.5 ml 200 X neutral red
   (2) Colorless Medium (CM)

| 2 × CMO | 100 ml |
|---|---|
| $H_2O$ | 60 ml |
| 10 × Earle's BSS | 20 ml |
| 50 × MEM Amino Acids | 4 ml |
| 100 × MEM nonessential Amino Acids | 2 ml |
| 100 × MEM vitamins | 2 ml |
| 7.5% $NaHCO_3$ | 6 ml |
| 200 mM 1-glutamine | 4 ml |
| gentamicin (50 mg/ml) | 0.2 ml |

(3) Colorless 10 X Earle's Balanced Salt Solution
      i. Solution A: 2.64 gm $CaCl_2 \cdot 2H_2O$ per 100 ml $H_2O$
      ii. Solution B: 2.00 GM $MGSO_4 \cdot 7H_2O$ per 100 ml $H_2O$
      iii. Solution C: (per 750 ml $H_2O$):
      4.000 gm KCl
      68.000 gm NaCL
      1.400 gm $NaH_2PO_4$ $H_2O$
      10.000 gm glucose
      iv. Add Solution B to Solution C, then add Solution A to the mixture. Bring 1000 ml volume, sterilize by filtration (0.2 micron) and store cold.
   (4) Trypsin - sigma trypsin EDTA 10 X:
   Trypsin (1:250) 5 gm/liter
   EDTA 4 Na 2 gm/liter prepared in 0.9% NaCl
   Prepare 1 X solution in a $Ca^{++}$ and $Mg^{++}$ free balanced salt solution (PBS, HBSS). Add glucose 1.1 gm/liter.
   d. Incubate plates at 37° C. and read the following day. Antiviral activity should be observed from two parameters. One is actual reduction in the number of plaques and two is the diminution in plaque diameter.
3. Scoring Drug Activity
   a. Antiviral activity is scored from 0 to +++.
   +++ = complete inhibition of plaque formation
   ++ = partial inhibition
   + = partial inhibition
   +/− = marginal inhibition
   0 = no protection
   b. Cytotoxicity
   (1) Wells of 24 well tissue culture plates are 16 mm in diameter. Discs are 6 mm in diameter. Zones of cytotoxicity greater than 6 mm are graded from 8 to 16 using only even numbers.
   (2) 0 = no macroscopic or microscopic cytotoxicity. 16 = 100% toxicity or complete cell destruction. 8, 10, 12, 14 = Diameter of toxic zone including diameter of 6 mm disc.

Antiviral Assay for Mouse Coronavirus A-59

A. Cell Culture

NCTC clone 1469, a derivative of mouse liver, ATCC No. CCL 9.1$_8$ freeze 2518, passage no. 16.

B. Maintenance of Cell Culture

1. Subcultures are prepared by brief exposure to trypsin-EDTA mixture and shaking the flask hard to remove the cells.
2. Trypsinization
   a. Aseptically remove the medium.
   b. Add 4 ml of trypsin-EDTA mixture to a 150 cm$^2$ flask. Reduce volume if flasks are smaller.
   c. Leave for one minute or less and then shake flask.
   d. Add 10 ml of growth medium and break up cell clumps with pipetting.
   e. Count cells.
3. Subcultures for maintenance of cells for assays.
   a. Seed 150 cm$^2$ tissue culture flasks with $10 \times 10^6$ cells in 40 ml growth medium.
   b. Split cultures a minimum of twice a week.

C. Virus

Mouse hepatitis virus strain MHV-A59 is classified as a coronavirus, ATCC No. 764.

D. Preparation of Plates for Viral Assays

Cell concentration
   a. Dilute the cells with growth medium to between $5 \times 10^5$ and $7.5 \times 10^5$ cells per ml.
   b. Seed 24 well trays with 1.0 ml per well.
   c. In order for test to work and be easy to read the cell concentration must be heavy.
   d. Incubate at 37° C. with 5% CO$_2$
   e. The cells must be used in the next 24 hours for viral assays. If the cells are held for a longer period of time cells begin to shed into the medium and the CPE and cell fusion takes 48 hours and longer instead of 12 to 14 hours. Assay is not sensitive and results are not comparable for 24 and 48 hours.

E. Viral Assay

1. Dilute drug or extract for test in the appropriate solvent.
2. Add 20 lambda to a 12 mm by 75 mm glass tube for a 16 mm test well.
3. Allow the solvent to evaporate under a laminar flow hood.
4. Dilute the MHV-A59 in Dulbecco's phosphate buffered saline for Ca$^{++}$ and Mg$^{++}$ to the appropriate predetermined dilution for the lot number currently in use. Normally the dilution of virus in a titration which gives a 3+ to 4+ CPE in 24 hours is the dilution used in this assay.

5. Remove medium from wells of 24 well plate containing NCTC 1469 cells seeded earlier.

6. Add 200 lambda of diluted virus to each test well. Add PBS to control wells.

7. Incubate cells and virus for 1 hour at 37° C.

8. Pour off supernatant at end of incubation period.

9. To each glass tube add 10 lambda of dimethyl sulfoxide (DMSO). The purpose for the DMSO is to solubilize the drug. If it is known that the drug under test is water soluble then the DMSO is not necessary.

10. Add 1 ml of maintenance medium to each glass tube.

11. Pour the contents of the glass tube into the corresponding well of the tissue culture plate.

12. Incubate infected cells at 37° C. and read the following day.

13. At twelve hours areas of cell fusion are quite apparent and can be detected both visually and microscopically. 14. At 24 hours, the CPE is extensive and on stained plates the difference between activity and none is apparent from visual examination.

15. To stain plates discard medium and to each 16 mm well add 200 lambda of methylene blue stain or other appropriate stain.

16. Leave the stain on the cell sheet for 30 minutes or more.

17. Pour off the stain and wash plates in tap water until the water is clear.

18. Allow plates to dry. If it is desired the plates can be kept as a permanent record for the experiment.

19. Scoring drug activity a. Cytotoxicity scoring

100%=complete cell destruction

75%=partial cell destruction

50%=partial cell destruction

25%=partial cell destruction

0%=no cytotoxicity b. Antiviral activity is scored from 0 to +++

+++=complete inhibition of cytopathic effects and cell fusion

++=partial inhibition

+=partial inhibition

+/−=marginal inhibition

0=no protection

F. Media

1. Growth medium for NCTC 1469 cell line

Medium NCTC 135 (GIBCO Cat. #320-1350)

10% horse serum

2% 200 mM 1-glutamine

1% nonessential amino acids (NEAA) (100X)

1% sodium pyruvate (110 mg/liter) (100X)

gentamicin 10 mg/ml (use 50 μg/ml or 0.5 ml/100)

50 ug/ml (use 50 μg/ml or 0.1 ml/100)

2. Maintenance medium for viral assay:

Dulbecco's modified Eagle medium @4500 mg/L glucose GIBCO Cat. #320-1965

5% fetal bovine serum (FBS)

2% 200 mM 1-glutamine

1% nonessential amino acids (NEAA) (100X)

1% sodium pyruvate (110 mg/liter) (100X)

gentamicin (use 50 μg/ml)

3. Trypsin:

GIBCO Cat. #610-5405 trypsin-EDTA (10X)

5.0 gm trypsin (1:250) and 2.0 gm EDTA/L

Prepare 1 X solution in Dulbecco's phosphate buffered saline free of $Ca^{++}$ and $Mg^{++}$. Add 1.1 grams glucose per liter.

4. Stain:

Methylene Blue-certified

Sigma No. M 9140 ordered in 25 g quantity

50% ethanol:water 5 grams methylene blue/liter

This stain does not have to be filtered. It is highly soluble in this water alcohol mixture.

The antiviral profile indicates that the compositions of the invention as represented by diterpenes A and B, formulae I and II, are effective for controlling VSV, HSV-1 and A-59 in vitro in concentrations as low as 2.0 μg/ml. The results are indicative of the utility of the compositions of the invention to control viruses in vitro and in vivo in hosts both animal and plant, as well as the diseases caused by viruses.

The scope of the present invention is not limited by the description, examples, and suggested uses herein and modifications can be made without departing from the spirit of the invention. For example, it may be noted that other derivatives of the compositions of the example may possess antiviral activity analogous to those preferred embodiments described above.

Further, the compositions described herein may have other useful applications such as, for example, analgesic, antitumor or antibacterial applications.

Application of the compositions of the present invention can be accomplished by any suitable therapeutic method and technique as is presently or prospectively known to those skilled in the art. Therapeutic methods of the invention comprise the administration of antiviral effective amounts of one or more of the compounds of the invention as an active ingredient, together with desired pharmaceutically acceptable diluents, adjuvants and carriers, to an organism suffering from a virus induced disease state. Unit dosage forms of compounds administered according to the methods of the invention may be formulated by those skilled in the art to provide effective daily dosages that vary in accordance with body weight of the animal to be treated. Parenteral administration, and particularly intraperitoneal administration, are preferred routes for practice of the inventive methods. Thus, it is intended that the present invention cover the modifications and variations of this invention provided that they come within the scope of the appended claims and their equivalents.

What is claimed is:

1. An antiviral composition comprising as the active ingredient an antiviral effective amount of one or more diterpene compound of the formulae:

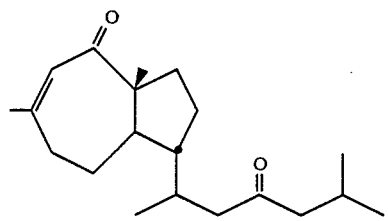

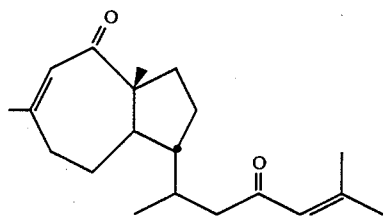

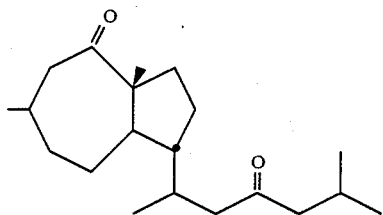

-continued

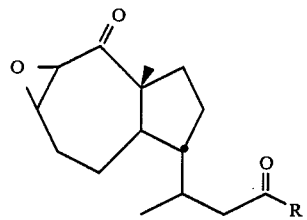

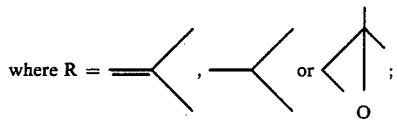

where R =

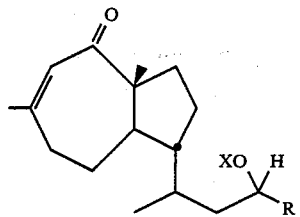

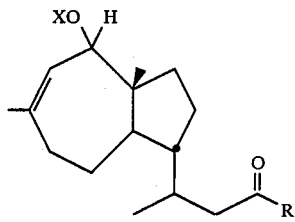

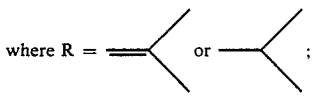

where R = and X = H or Ac; and

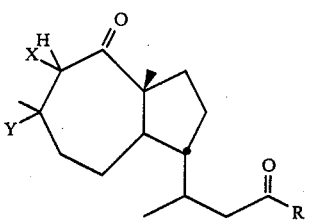

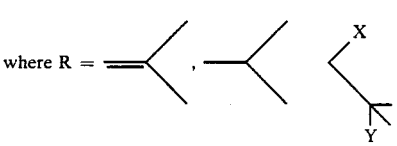

where R = and X, Y = Br, Cl, OH, or OAc; and pharmaceutically acceptable carrier.

2. An antiviral composition according to claim 1 wherein the active ingredient is the compound of the formula:

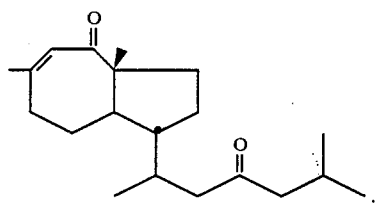
3. A method for inhibiting viruses in a host in need thereof comprising administering an antiviral effective amount of a diterpene compound comprising at least one compound of the formulae:
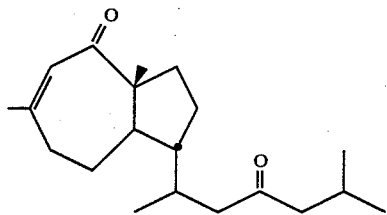
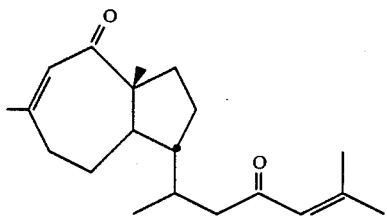
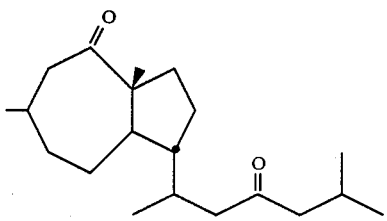
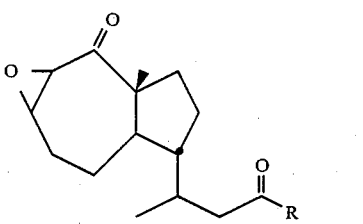
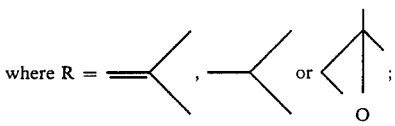
where R = 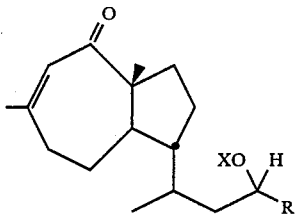 ;
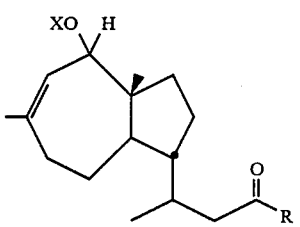
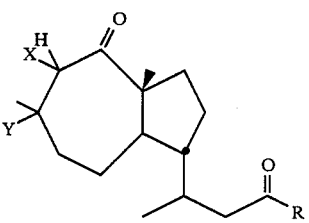
where R = 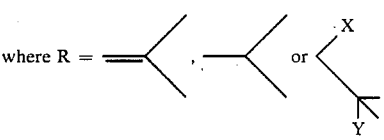 ;
and X = H or Ac; and
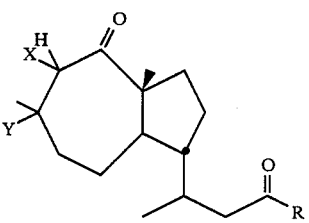
where R = 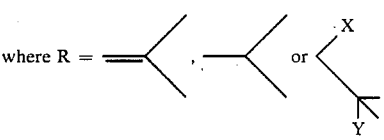
and X, Y = Br, Cl, OH, or OAc.
4. A method for inhibiting viruses according to claim 3 wherein the is a mammalian host.
* * * * *

UNITED STATES PATENT AND TRADEMARK OFFICE
CERTIFICATE OF CORRECTION

PATENT NO. : 4,935,439

DATED : June 19, 1990

INVENTOR(S) : Yoel Kashman, Shulamit Hirsch, Sue S. Cross, Frank Koehn

It is certified that error appears in the above-identified patent and that said Letters Patent is hereby corrected as shown below:

Title Page: *"Attorney, Agent or Firm*—Saliwanchik & Saliwanchik" should read --*Attorney, Agent or Firm*—Saliwanchik & Saliwanchik; Carroll Palmer--.

Column 1: line 12: "Epipolasis" should read --Epipolasis.--

Column 6: line 17: "however Suitable" should read --however. Suitable--.

Column 8: line 5: "47.0T" should read --47.0t--.

Column 10: line 3: "solution" should read --solution:--.

Column 14: line 6:

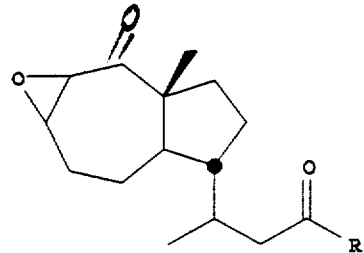 should read 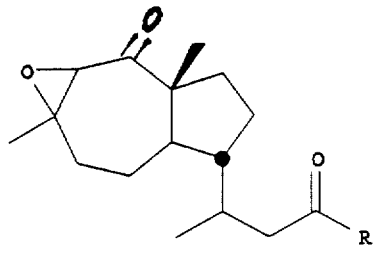

UNITED STATES PATENT AND TRADEMARK OFFICE
CERTIFICATE OF CORRECTION

PATENT NO. : 4,935,439

DATED : June 19, 1990

INVENTOR(S) : Yoel Kashman, Shulamit Hirsch, Sue S. Cross, Frank Koehn

It is certified that error appears in the above-identified patent and that said Letters Patent is hereby corrected as shown below:

Column 15: line 49:

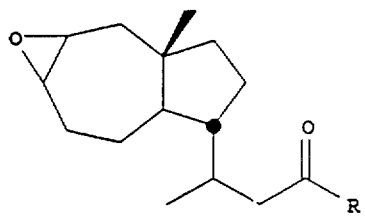   should read   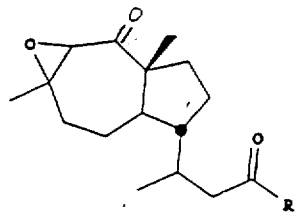

Signed and Sealed this

Twelfth Day of May, 1992

Attest:

DOUGLAS B. COMER

Attesting Officer

Acting Commissioner of Patents and Trademarks